United States Patent
Eidenschink et al.

(10) Patent No.: US 11,998,183 B2
(45) Date of Patent: Jun. 4, 2024

(54) OCCLUDER WITH ACCESS PASSAGE AND CLOSURE THEREOF

(71) Applicant: St. Jude Medical, Cardiology Division, Inc., St. Paul, MN (US)

(72) Inventors: Tracee Eidenschink, Wayzata, MN (US); Andrea Stafford, New Brighton, MN (US); Brian Perszyk, Shoreview, MN (US); Theodore P. Dale, Corcoran, MN (US); Luann Raposo, Discovery Bay, CA (US); Alex Bloomquist, Mound, MN (US); Michael P. Meyer, Minnetrista, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 18/493,558

(22) Filed: Oct. 24, 2023

(65) Prior Publication Data
US 2024/0050080 A1    Feb. 15, 2024

Related U.S. Application Data

(63) Continuation of application No. 17/856,553, filed on Jul. 1, 2022, which is a continuation of application
(Continued)

(51) Int. Cl.
*A61B 17/00*    (2006.01)
*A61B 17/34*    (2006.01)
*A61B 90/00*    (2016.01)

(52) U.S. Cl.
CPC ............... *A61B 17/0057* (2013.01); *A61B 2017/00004* (2013.01); *A61B 2017/00526* (2013.01);
(Continued)

(58) Field of Classification Search
CPC ...... A61B 17/0057; A61B 2017/00004; A61B 2017/00526; A61B 2017/00575;
(Continued)

(56) References Cited

U.S. PATENT DOCUMENTS 10,265,059 B2    4/2019    Rowe
10,799,245 B2    10/2020   Zhang
(Continued)

FOREIGN PATENT DOCUMENTS

WO    2018204106 A1    11/2018

OTHER PUBLICATIONS

European Search Report for corresponding EP Patent Application No. 20192944.5, dated May 19, 2021, 10 pages.

*Primary Examiner* — Mohamed G Gabr
(74) *Attorney, Agent, or Firm* — SLEMAN & LUND LLP

(57) ABSTRACT

The present disclosure is directed to embodiments of an occlusive medical device including a frame and at least one closure coupled to the frame. The frame includes a distal annular flange having a radially outer surface and a radially inner surface, a proximal annular flange having a radially outer surface and a radially inner surface, and a waist portion extending between and connecting the distal annular flange to the proximal annular flange. The radially inner surface of the distal annular flange, the waist member, and the radially inner surface of the proximal annular flange define an unobstructed passageway through the frame. The at least one closure is configured to close the passageway to: (i) provide an occlusive effect, and (ii) enable subsequent access through the passageway.

19 Claims, 18 Drawing Sheets

Related U.S. Application Data

No. 17/003,280, filed on Aug. 26, 2020, now Pat. No. 11,832,805.

(60) Provisional application No. 62/891,542, filed on Aug. 26, 2019.

(52) U.S. Cl.
CPC ............ *A61B 2017/00606* (2013.01); *A61B 2017/00623* (2013.01); *A61B 2017/00867* (2013.01); *A61B 2017/00884* (2013.01); *A61B 2017/3425* (2013.01); *A61B 2090/3966* (2016.02)

(58) Field of Classification Search
CPC .......... A61B 2017/00592; A61B 2017/00597; A61B 2017/00606; A61B 2017/00623; A61B 2017/00867; A61B 2017/00884; A61B 2017/3425; A61B 2090/3966; A61M 39/0247

See application file for complete search history.

(56) References Cited

U.S. PATENT DOCUMENTS

| | | |
|---|---|---|
| 10,898,698 B1 | 1/2021 | Eigler |
| 11,045,178 B2 | 6/2021 | Onushko |
| 11,071,533 B2 | 7/2021 | Rothstein |
| 2001/0054519 A1 | 12/2001 | Nishiwaki |
| 2009/0216264 A1 | 8/2009 | Friedman |
| 2011/0054519 A1 | 3/2011 | Neuss |
| 2012/0283768 A1* | 11/2012 | Cox ................... A61B 17/1219 606/198 |
| 2016/0338706 A1* | 11/2016 | Rowe ................ A61B 17/0057 |
| 2017/0079631 A1 | 3/2017 | Ferrari |
| 2017/0224323 A1 | 8/2017 | Rowe |
| 2018/0333150 A1* | 11/2018 | Bak-Boychuk .... A61B 17/0057 |
| 2019/0046170 A1* | 2/2019 | Coyle ................ A61B 17/0057 |
| 2019/0209180 A1 | 7/2019 | Kealey |
| 2019/0282746 A1 | 9/2019 | Judisch |
| 2021/0236138 A1 | 8/2021 | Perszyk |
| 2021/0290214 A1 | 9/2021 | Cole |

* cited by examiner

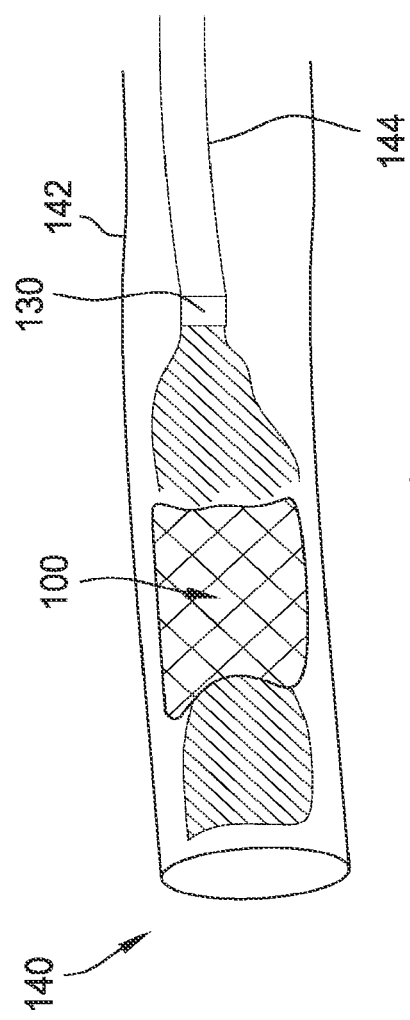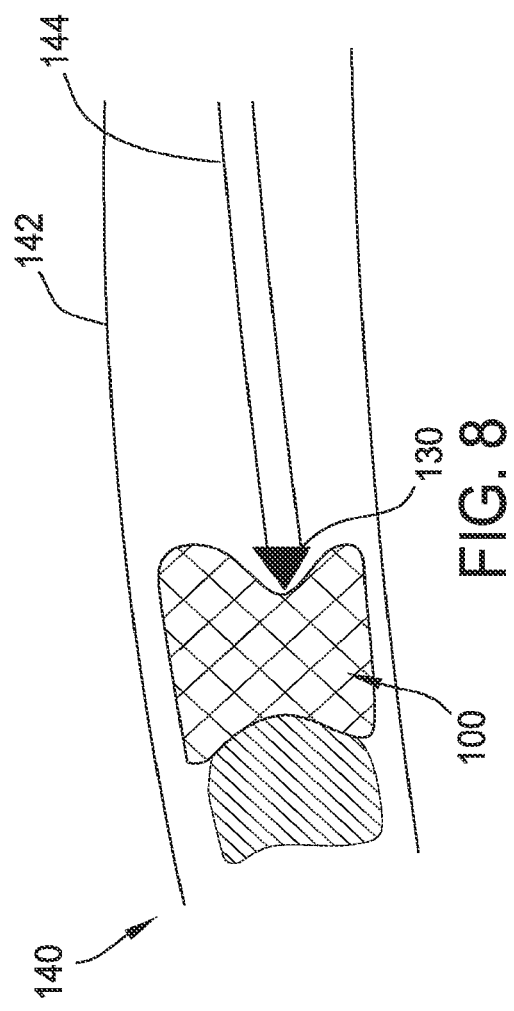
FIG. 7
FIG. 8

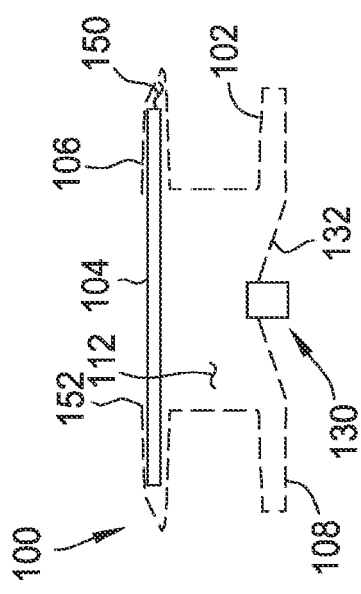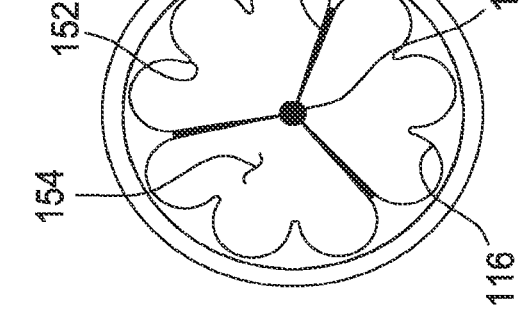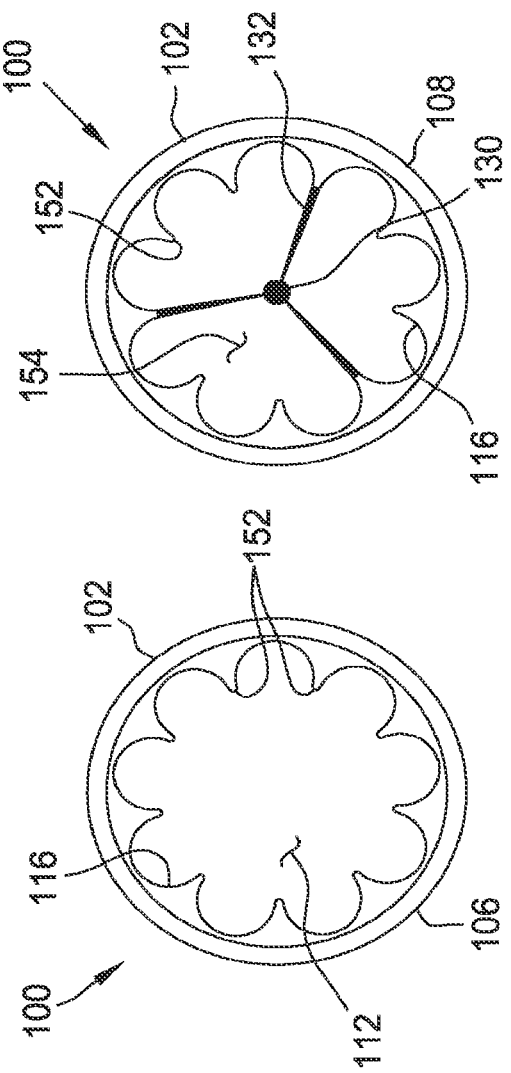

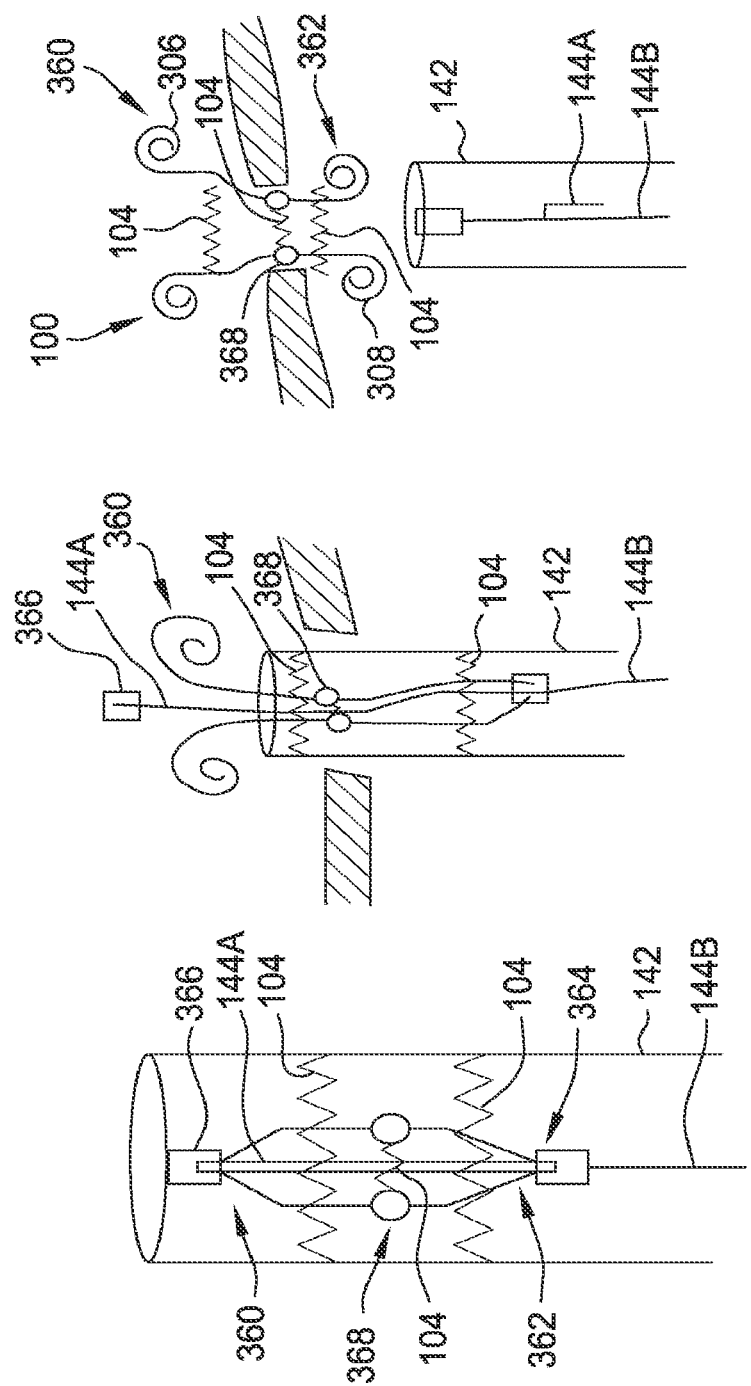

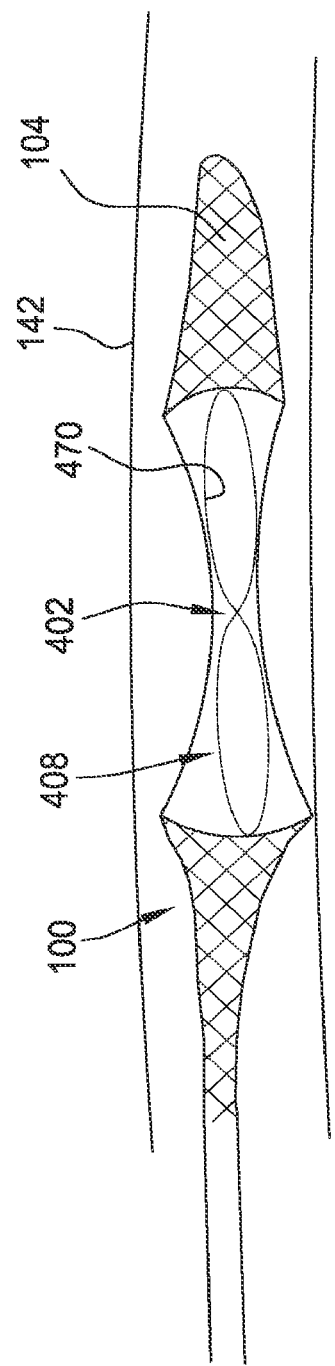

OCCLUDER WITH ACCESS PASSAGE AND CLOSURE THEREOF

CROSS-REFERENCE TO RELATED APPLICATIONS

The present application is a continuation of U.S. patent application Ser. No. 17/856,553, filed Jul. 1, 2022, which is a continuation of U.S. patent application Ser. No. 17/003,280, filed Aug. 26, 2020, which claims the benefit of priority to U.S. Provisional Patent Application No. 62/891,542, filed Aug. 26, 2019, the entire contents and disclosures of which are hereby incorporated by reference herein.

BACKGROUND OF THE DISCLOSURE

A. Field of the Disclosure

The present disclosure relates generally to medical devices that are used in the human body. In particular, the present disclosure is directed to embodiments of a closure device or occluder that includes an access passage and at least one closure of the access passage, and methods of making and using the same. The embodiments and methods disclosed herein enable access through the occluder subsequent to deployment of the occluder within the body.

B. Background

Atrial Septal defects (ASD) include heart defects that allow blood to flow between the left and right atria of the heart, decreasing cardiac output. In at least some cases, ASD are closed using an occlusive closure device, such as the Amplatzer™ Septal Occluder (ASO). Occluders are generally formed from braided metal fabrics or wire with mesh. Some of these known occluders are shown in FIG. 1. As illustrated, conventional occluders 50 are formed with discs 52 that engage a surface of the septal wall that separates the left and right atria. These discs 52 can range in size from 10 mm to 54 mm in diameter and are conventionally formed of continuous metal fabric or wire. As such, these discs 52 form a substantially impenetrable surface, in particular for smaller-size occluders 50.

Several percutaneous procedures, which may be performed after an occluder has been deployed, require access to the left atrium across the septal wall. For example, a younger patient may have an occluder deployed to close an ASD, but may subsequently develop atrial fibrillation (AFIB). A physician may need to map and/or ablate tissue in the left atrium, and may therefore need to cross the septal wall. Where a conventional occluder has already been deployed, the physician may be unable to penetrate the discs (e.g., discs 52 shown in FIG. 1) to cross the septal wall at the existing opening therethrough (i.e., the ASD).

Accordingly, it would be desirable to have an occlusive closure device that enables subsequent access for passage of medical devices therethrough, including procedural devices and/or devices to create shunting and/or fenestrations Moreover, a rare, but adverse event that has been reported to occur in some occluder implantations is erosion of the atrial wall tissue. The result of this tissue erosion can be removing the device, fixing eroded holes and/or surgically closing defects.

Accordingly, it would be desirable to reduce or eliminate erosion of cardiac tissue while maintaining the fundamental function and effectiveness of an occluder.

BRIEF SUMMARY OF THE DISCLOSURE

The present disclosure generally relates to a closure device or occluder including an access passage. The present disclosure discloses such devices and methods of forming and using the same to, for example, enable access for medical devices therethrough after the closure device has been deployed in the human body. The occluder having the access passage further facilitates reducing erosion of cardiac tissue by reducing radial forces applied thereto.

In at least one aspect of the present disclosure, an occlusive medical device is provided. The occlusive medical device includes a frame and at least one closure coupled to the frame. The frame includes a distal annular flange having a radially outer surface and a radially inner surface, a proximal annular flange having a radially outer surface and a radially inner surface, and a waist portion extending between and connecting the distal annular flange to the proximal annular flange. The radially inner surface of the distal annular flange, the waist member, and the radially inner surface of the proximal annular flange define an unobstructed passageway through the frame. The at least one closure is configured to close the passageway to: (i) provide an occlusive effect, and (ii) enable subsequent access through the passageway when the occlusive medical device is deployed at a target site.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 7 depicts one exemplary embodiment of the occluder disposed within a delivery system in accordance with the present disclosure.

FIG. 8 depicts another exemplary embodiment of the occluder disposed within a delivery system in accordance with the present disclosure.

FIGS. 9A-9C illustrate another exemplary embodiment of the occluder in accordance with the present disclosure, the occluder including an internal closure.

FIGS. 16A-16C illustrate deployment of the occluder shown in FIG. 15.

FIG. 18 illustrates the occluder shown in FIGS. 17A and 17B disposed within a delivery device.

Corresponding reference characters indicate corresponding parts throughout the several views of the drawings. It is understood that that Figures are not necessarily to scale.

DETAILED DESCRIPTION OF THE DISCLOSURE

Figure 1:
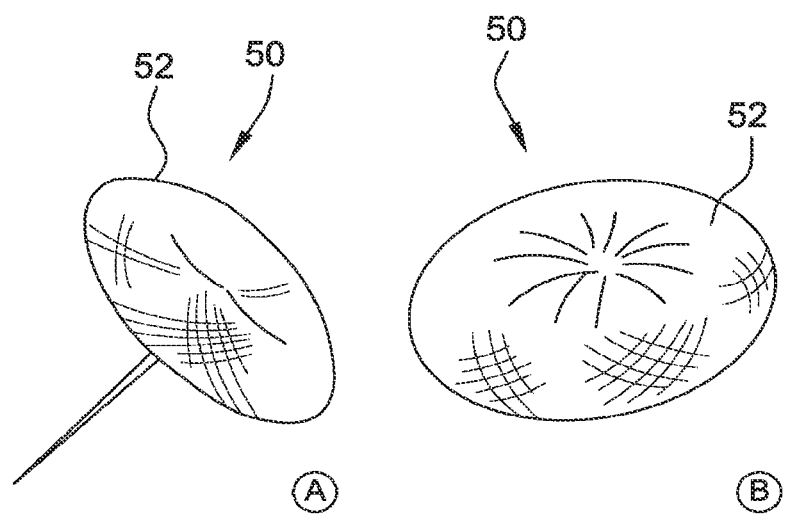
FIG. 1 illustrates embodiments of conventional occluders.

The present disclosure relates generally to medical devices that are used in the human body. In particular, the present disclosure generally relates to occluders including an access passage for access through the occluder (e.g., by a medical device) subsequent to deployment of the occluder within a patient's body. The occluders also include a closure that serves an occlusion function but that is penetrable to allow access through the access passage. As used herein, "access" refers broadly to access to and/or through the access passage by any medical device performing any function. Accordingly, "access" may refer to access by a medical device such as a catheter that is passed completely through the occluder, as well as to access by a medical device such as a device configured to create a fenestration in the occluder (e.g., a dilator, balloon, etc.).

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

Some embodiments of the present disclosure provide a medical device, such as an occlusion device (occluder), for use in occluding an abnormality in a patient's body, such as an Atrial Septal Defect (ASD), a Ventricular Septal Defect (VSD), a Patent Ductus Arteriosus (PDA), a Patent Foramen Ovale (PFO), conditions that result from previous medical procedures such as Para-Valvular Leaks (PVL) following surgical valve repair or replacement, and the like. The device may also be used as a flow restrictor, pressure release device, or an aneurysm bridge or other type of occluder for placement in the vascular system. It is understood that the use of the term "abnormality" is not meant to be limiting, as the device may be configured to occlude any vessel, organ, opening, chamber, channel, hole, cavity, or the like, located anywhere in the body.

Some embodiments of the present disclosure provide an improved percutaneous catheter directed intravascular occlusion device for use in the vasculature in patients' bodies, such as blood vessels, channels, lumens, a hole through tissue, cavities, and the like, such as an ASD or VSD. Other physiologic conditions in the body occur where it is also desirous to occlude a vessel or other passageway to prevent blood flow into or therethrough. These device embodiments may be used anywhere in the vasculature where the anatomical conditions are appropriate for the design.

The medical device may include one or more occlusive materials, which are configured to substantially preclude or occlude the flow of blood so as to facilitate thrombosis. As used herein, "substantially preclude or occlude flow" shall mean, functionally, that blood flow may occur for a short time, but that the body's clotting mechanism or protein or other body deposits on the occlusive material results in occlusion or flow stoppage after this initial time period. According to one embodiment of the present disclosure, the device is configured to occlude at least a portion of a vessel, a channel, a lumen, an opening, or a cavity in less than about 10 minutes and even less than about 5 minutes with observed occlusions in testing as low as within about 1 minute. Thus, in one embodiment, there is not "immediate occlusion," as the device does not immediately obstruct all blood flow but, rather, slows the flow of blood in order for occlusion to occur as described above. Such immediate occlusion may result in problems in fixation or positioning of the device in the lumen or may result in suction or the complete stoppage of flow which may be undesirable in some circumstances.

Figure 2A:
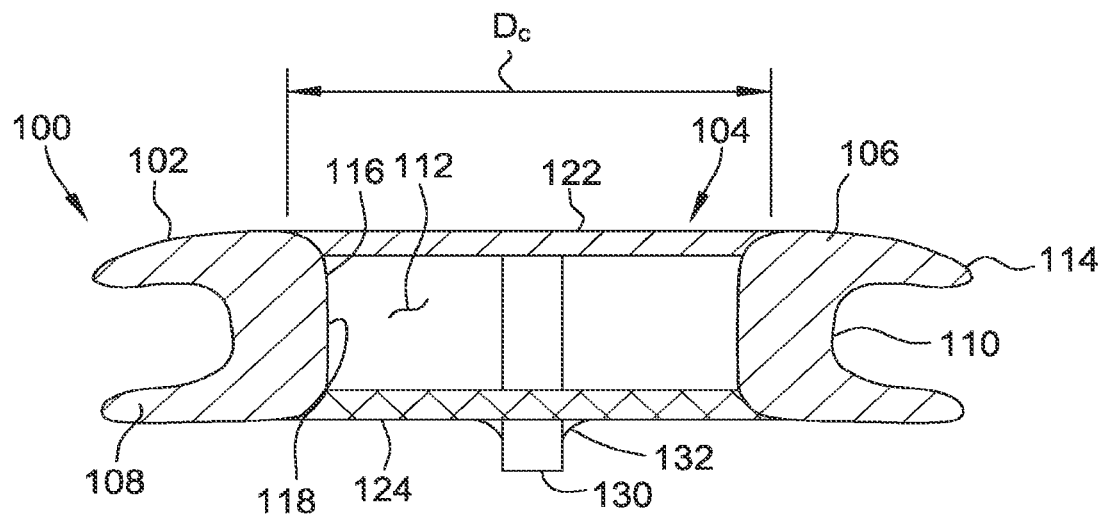
FIGS. 2A and 2B illustrate an exemplary embodiment of an occluder including an access passage sealed by an occlusive but penetrable closure in accordance with the present disclosure.
Figure 2B:
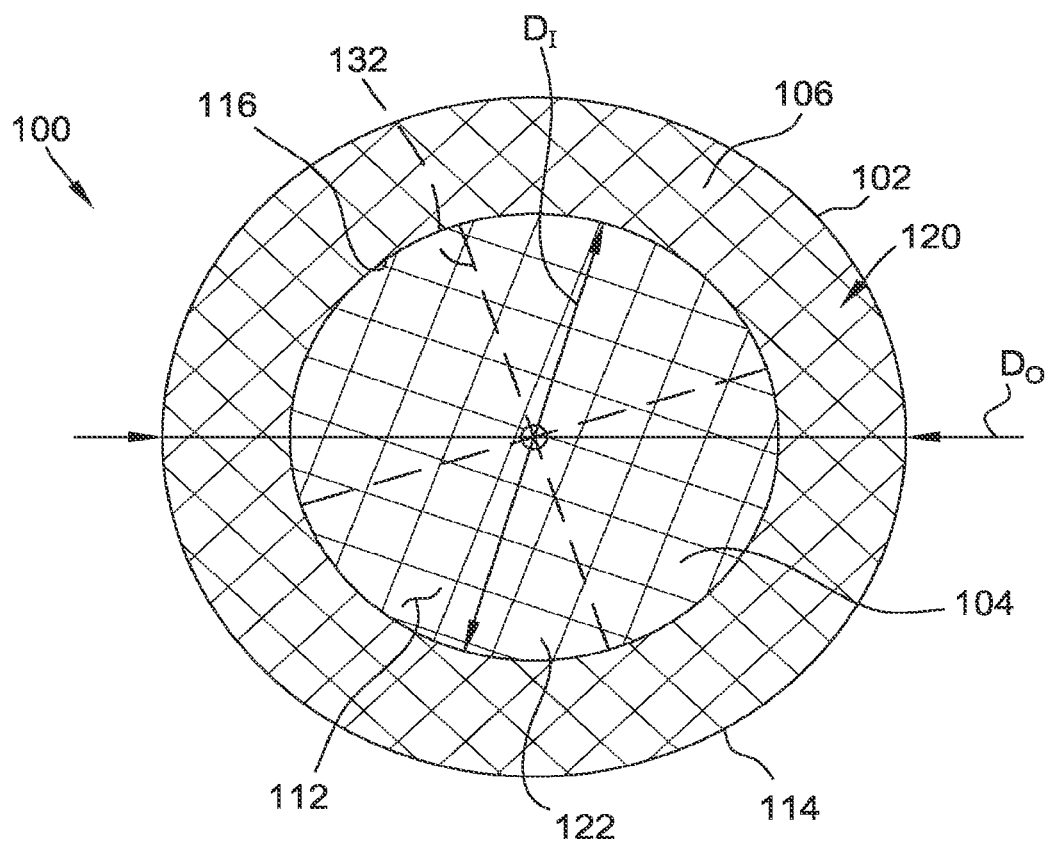

FIGS. 2A and 2B, by way of example, illustrate an exemplary embodiment of a medical device 100 in accordance with the present disclosure. The medical device 100 is specifically embodied as an occluder. The occluder 100 includes a frame 102 and at least one closure 104. More particularly, the frame 102 has an outer shape such that, when the occluder 100 is deployed, the frame 102 conforms to the tissue (not shown in FIGS. 2A and 2B) in which the occluder 100 is deployed.

In one embodiment, the frame 102 includes two annular flanges 106, 108, specifically a left atrial or distal flange 106 and a right atrial or proximal flange 108. The annular flanges 106, 108 are connected by a waist member 110. The occluder 100 defines an open or substantially open passageway 112 that extends through the occluder 100. Specifically, the passageway 112 extends through the distal annular flange 106, the waist member 110, and the proximal annular flange 108. The annular flanges 106, 108 therefore have a radially outer surface 114 with an outer diameter $D_O$ and a radially inner surface 116 with an inner diameter $D_I$, where the radially inner surface 116 partially defines the passageway 112 (and generally corresponds to an inner surface 118 of the waist member 110). In this way, annular flanges 106, 108 are considered "open," as contrasted with closed discs (e.g., discs 52, shown in FIG. 1).

When the occluder 100 is deployed to occlude a defect (e.g., an ASD, VSD, and the like), as described further herein, the occluder 100 is positioned within a hole in the septal wall. The distal annular flange 106 is positioned on a distal side of the septal wall (i.e., within the left atrium) and engages a distal surface of the septal wall. The proximal annular flange 108 is positioned on a proximal side of the septal wall (i.e., within the right atrium) and engages a proximal surface of the septal wall. The waist member 110 extends between and connects the annular flanges 106, 108. An outer surface of the waist member 110 engages and conforms to a surface of the ASD. The occluder 100 is radially flexible but still exerts a suitable clamping force to maintain engagement and conformity with the local tissue, which may reduce the risk of erosion. Each of the annular flanges 106, 108 and the waist member 110 exhibit radial flexibility and improved conformance with local tissue, as compared to conventional occluders.

The outer diameter $D_O$ of the annular flanges 106, 108 is greater than a diameter of the ASD in which the occluder 100 is deployed, and the inner diameter $D_I$ is less than the outer diameter $D_O$. In some embodiments, the inner diameter $D_I$ is sized such that the occluder 100, specifically the passageway 112, may enable access therethrough of delivery devices having sizes from 4 French (Fr) to 36 Fr. It should be readily understood that the outer diameter $D_O$ and/or the inner diameter $D_I$ may vary based on the overall size of the occluder 100 and/or the defect (e.g., the ASD) in which the occluder 100 is to be deployed, which may limit the size of medical devices that may be maneuvered through passageway 112.

In some embodiments, $D_O$ is about 5 mm to about 20 mm larger than $D_I$. In some embodiments, the ratio of the area defined by the radially outer surface 114 (i.e., $\pi*(\frac{1}{2} D_O)^2$) and the area defined by the radially inner surface 116 (i.e., $\pi*(\frac{1}{2} D_I)^2$) is about 2:1, such that the passageway 112 (partially defined by the radially inner surface 116) constitutes about 50% of a surface area of a respective planar face 120 defined by each annular flange 106, 108. It should be well understood that the passageway 112 may constitute more or less than 50% of the surface area of this planar face, as long as the passageway 112 is sufficiently sized to enable access therethrough to various medical devices, such as catheters. In the exemplary embodiment, the passageway 112 constitutes from about 20% to about 90% of the surface area of each annular flange 106, 108, and, more preferably, may constitute from about 50% to about 70% of the surface area of each annular flange 106, 108.

By forming the frame 102 with annular flanges 106, 108 (contrasted with closed discs, such as discs 52), the frame 102 may experience reduced radial hoop stress (e.g., due to the relative lack of rigid metal material in the center thereof). As such, the occluder 100 may exert less radial force on local tissue when the occluder 100 is deployed. Accordingly, the occluder 100 may reduce the risk of erosion of the local tissue compared to conventional occluders. Moreover, the reduction in material in the frame 102 may reduce production cost of the occluder 100.

The frame 102 may be formed from any suitable material. In at least some exemplary embodiments, the frame 102 is formed from at least one layer of braided metal material. In particular, the frame 102 is formed from a shape memory material, such as nitinol. In some embodiments, the frame 102 is formed from one or multiple layers of braided nitinol wires—for example, by folding one layer over itself to form two layers. Such a material may include, in some embodiments, from 36 to 288 wires. The frame 102 may be formed from non-braided materials, including shape memory alloys. For example, a shape memory alloy may be laser-cut and heat-set, or at least one formed wire (e.g., from 1 to 50 such wires) may be wrapped about a mandrel and heat-set. In some embodiments, a helical angle formed by the wire(s) of the frame 102 (e.g., braided and/or wound formed wires) may be selected to optimize a hoop strength and clamping force of the frame 102. This optimization may further reduce the radial force applied to local tissue when the occluder 100 is deployed, as described above.

Alternatively, the frame 102 is formed from a non-shape memory material and may be deployed using a balloon expander. In such embodiments, the frame 102 may be formed from cobalt, stainless steel, chromium, and/or other such medical-grade metallic materials. Alternatively, the frame 102 may be formed from a polymeric material, such as plastic (e.g., injection-molded plastic, bioabsorbable polymers or plastics, etc.). It is contemplated that having a radiopaque (e.g., metallic, radiopaque plastic, etc.) and/or echogenic frame may facilitate more accurate deployment and/or subsequent identification of the location of the occluder 100.

Figure 3:
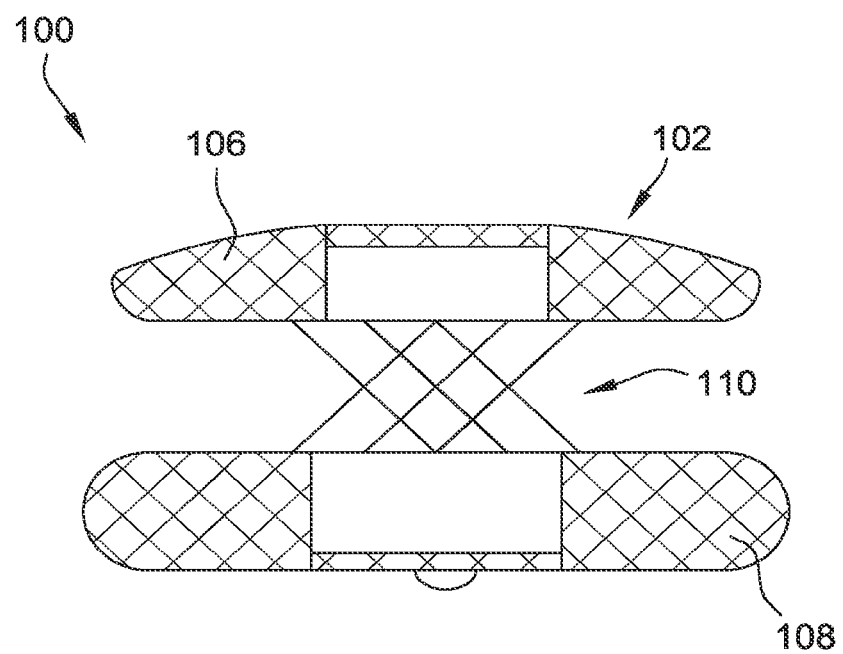
FIG. 3 illustrates an alternative embodiment of the occluder shown in FIGS. 2A and 2B including a non-unitary frame.

In the embodiment illustrated in FIGS. 2A and 2B, the frame 102 is a unitary, single-piece frame in which the annular flanges 106, 108 are integral with the waist member 110. In such embodiments, the frame 102 may be formed from a single material. In other embodiments, such as the embodiment illustrated in FIG. 3, the annular flanges 106, 108 are formed separately from the waist member 110 and are subsequently attached to the waist member 110 to form the frame 102. The waist member 110, in some embodiments, is the same material as the annular flanges 106, 108, but in other embodiments, the waist member 110 is formed from a different material than the annular flanges 106, 108. The waist member 110 may be attached to the annular flanges 106, 108 by sutures or sewing, welding, fasteners, adhesives, over-molding, insert molding, and/or any other suitable attachment method.

In the exemplary embodiment of the occluder 100, the at least one closure 104 is attached to the frame 102 to close or restrict access (e.g., of bodily fluids) through the passageway 112 of the occluder 100. In this way, the closure 104 ensures the occluder 100 performs its occlusive function, as described above herein. However, the closure 104 is formed from an occlusive, yet penetrable material, such that access through the passageway 112 of the occluder 100 by medical devices is not restricted. In the exemplary embodiment, a "penetrable" material is more easily punctured, separated, slit, pierced, or otherwise penetrated than the material that forms the frame 102.

In the illustrated embodiment of FIGS. 2A and 2B, the closure 104 includes a first or distal closure 122 and a second or proximal closure 124. The distal closure 122 is attached to the distal annular flange 106 at the radially inner surface 116 thereof. Likewise, the proximal closure 124 is attached to the proximal annular flange 108 at the radially inner surface 116 thereof. In this way, each closure 122, 124 closes passageway 112.

Each closure 122, 124 is sized and shaped to substantially cover the passageway 112 at each annular flange 106, 108. The closures 122, 124 may therefore be circular and have a diameter $D_C$ that is greater than or substantially equal to the inner diameter $D_I$ of the respective annular flange 106, 108 to which it is coupled. Closures 104 (including closures 122, 124), as described further herein, may have a diameter $D_C$ that is substantially greater than the inner diameter $D_I$. For example, the diameter $D_C$ may be greater than or substantially equal to the outer diameter $D_O$ of the respective annular flange 106, 108 to which it is coupled. Alternatively, the closure 104 may have a non-circular shape.

Figure 4:
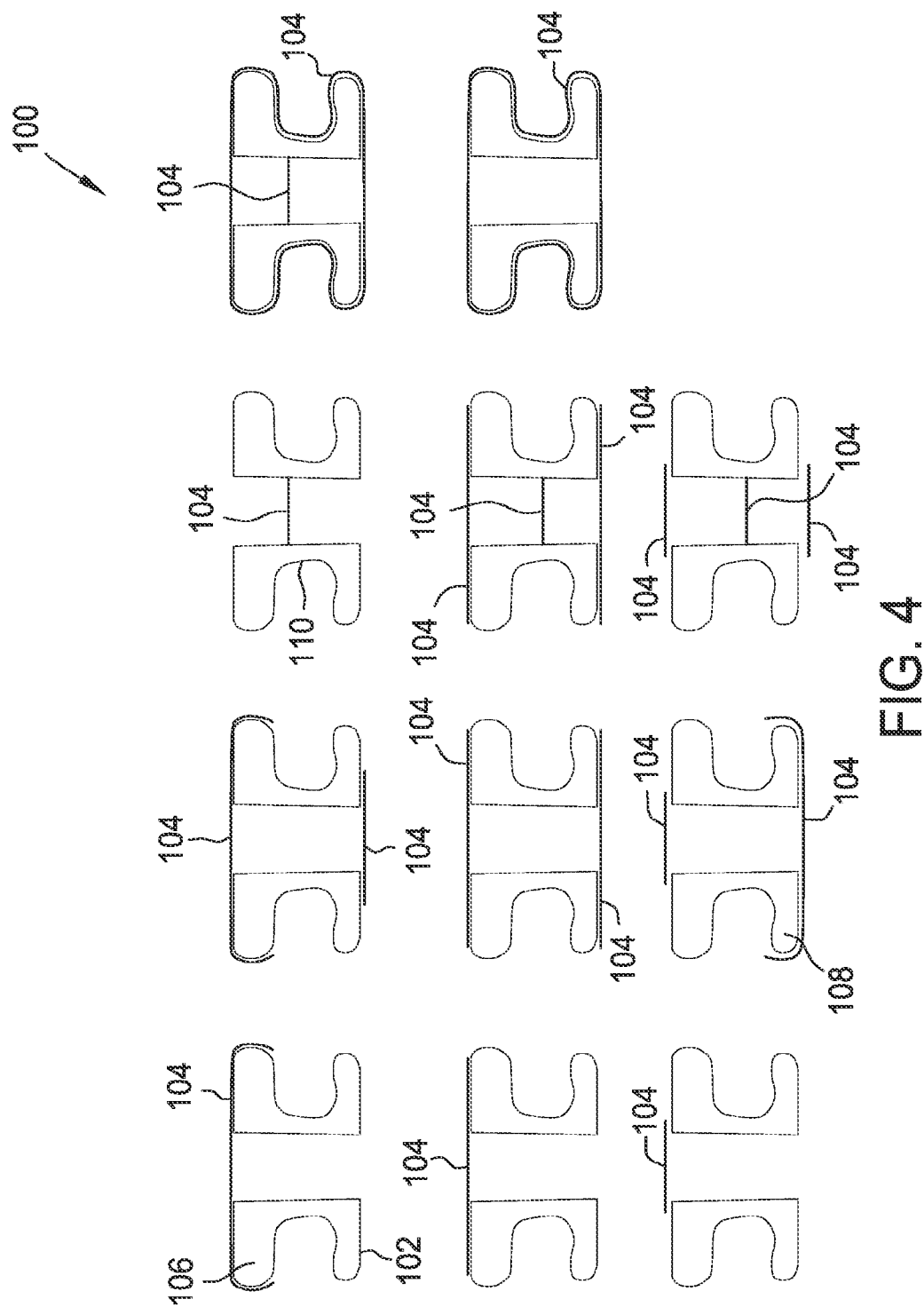
FIG. 4 depicts exemplary embodiments of the position of the closure of the occluder.

In particular, FIG. 4 illustrates various sizes, shapes, and locations of closures 104 with respect to the frame 102 of the occluder 100. The occluder 100 may include one, two, or three discrete closures 104. A closure 104 may be coupled to a flange at any location on an outer surface of the respective flange, such as adjacent the passageway 112, at the outer diameter of the flange, at some intermediate location, and/or at a surface of the flange that engages with the septal wall when the occluder 100 is deployed. A closure 104 may additionally or alternatively be coupled to the waist member 110 of the occluder 100 at a position intermediate the annular flanges 106, 108. A closure 104 may additionally or alternatively fully enclose the occluder 100.

A closure 104 is attached to the frame 102 using any suitable method, such as by suture or sewing, bonding (with other polymers, thermally, via laminating, etc.), welding, adhering, folding and/or trapping the closure 104 within the material of the frame 102, over-molding, any combination thereof, and/or any other suitable attachment mechanism. In the exemplary embodiment, therefore, the closure 104 is operable in tandem with the frame 102 during deployment (including loading, advancement, and/or recapture, as described further herein) of the occluder 100, such that the closure 104 collapses and expands as the frame 102 collapses expands.

The closure 104 may be formed from any suitable material. It is contemplated that a bioabsorbable material that promotes endothelialization may be used to form the closure 104. After the occluder 100 is deployed, the bioabsorbable material will be absorbed while tissue grows over the occluder 100. Therefore, the passageway 112 will be accessible through a relatively soft, thin layer of tissue. Such bioabsorbable materials may include polylactic acid (PLA), poly-L-lactic acid (PLLA), poly lactic-co-glycolic acid (PLGA), polycaprolactone (PCL), combinations thereof, and/or any suitable bioabsorbable material. Alternatively, the closure 104 is at least partially non-bioabsorbable, and may be formed from polyester, polyethylene terephthalate (PET), silicone, urethane, combinations thereof, other polymers, and the like. The closure 104 may, in some embodiments, be formed in part with a bioabsorbable material and in part with a non-bioabsorbable material. The closure 104 may be formed from a woven, knitted, or braided material, a printed material, a molded material, and the like. The closure 104 may be formed from a material suitable to form a fenestration therein, after the occluder 100 is deployed. For example, a medical device configured to create a fenestration (e.g., a dilator, a balloon expander, etc.) may be used to penetrate the closure 104 and create a fenestration therein (e.g., to enable blood flow through the occluder 100). The closure 104 may be formed from a material that will remain open after such a procedure.

In some embodiments, the closure 104 is flexible, which may simplify deployment of the occluder, as described further herein, and which may improve the penetrability of the closure 104 (contrasted with the more rigid, dense nitinol mesh that forms discs 52). In certain embodiments, however, the closure 104 may include one or more rigid reinforcement elements (not shown). These reinforcement elements may assist deployment of the occluder 100 by ensuring proper orientation of the closure 104 as the occluder 100 is deployed. In some such embodiments, the reinforcement elements are not bioabsorbable. In other embodiment, the reinforcement elements are bioabsorbable at a different rate than the flexible portion(s) of the closure 104.

In the illustrated embodiment, the occluder 100 also includes an attachment member 130. The attachment member 130 facilitates deployment of the occluder 100. As described further herein, the attachment member 130 is coupled to a delivery cable to advance the occluder 100 through a delivery catheter to a target location (e.g., an ASD). The attachment member 130 remains coupled to the delivery cable until proper positioning of the occluder 100 is confirmed. That is, the attachment member 130 facilitates re-positioning and/or recapture of the occluder 100 during deployment. The attachment member 130 may include a screw-like member having internal or external threads, a tether-like member, a hoop, a hook, a ball-and-loop type coupler, and/or any suitable attachment member 130 such that the occluder 100 is recapturable during deployment. The attachment member 130 may be formed from a bioabsorbable material.

Figure 5B:
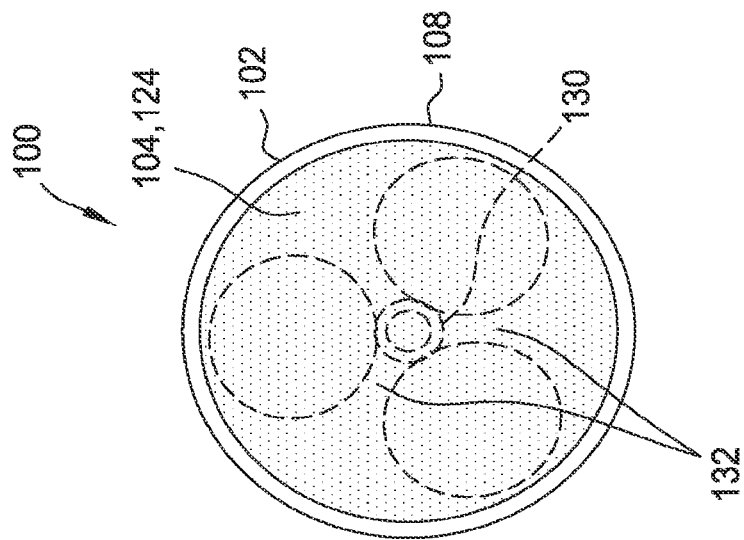
FIGS. 5A and 5B illustrate another exemplary embodiment of the occluder of the present disclosure including an attachment point for deployment and/or recapture of the occluder.
Figure 5A:
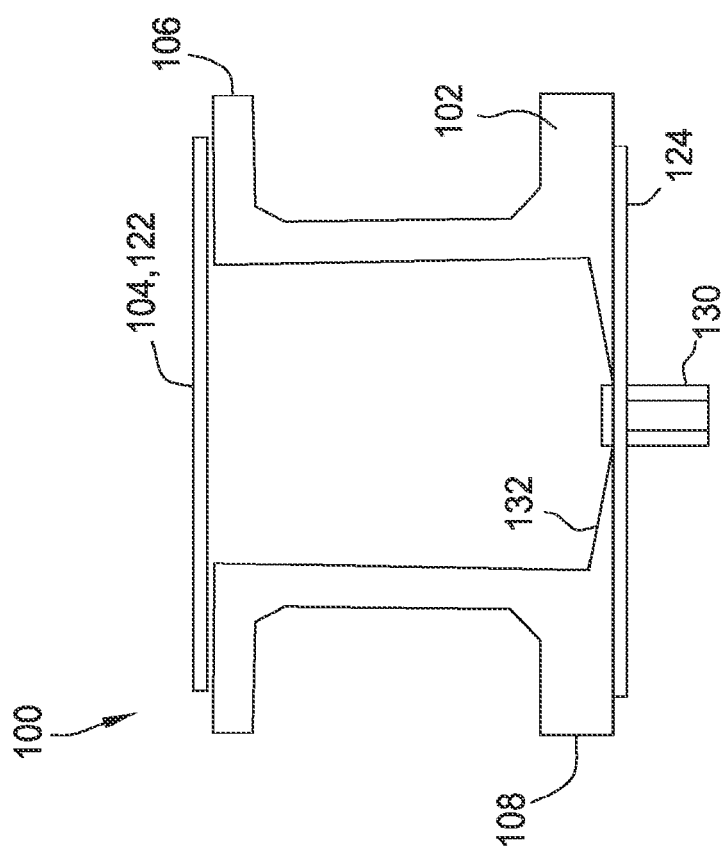
Figure 6:
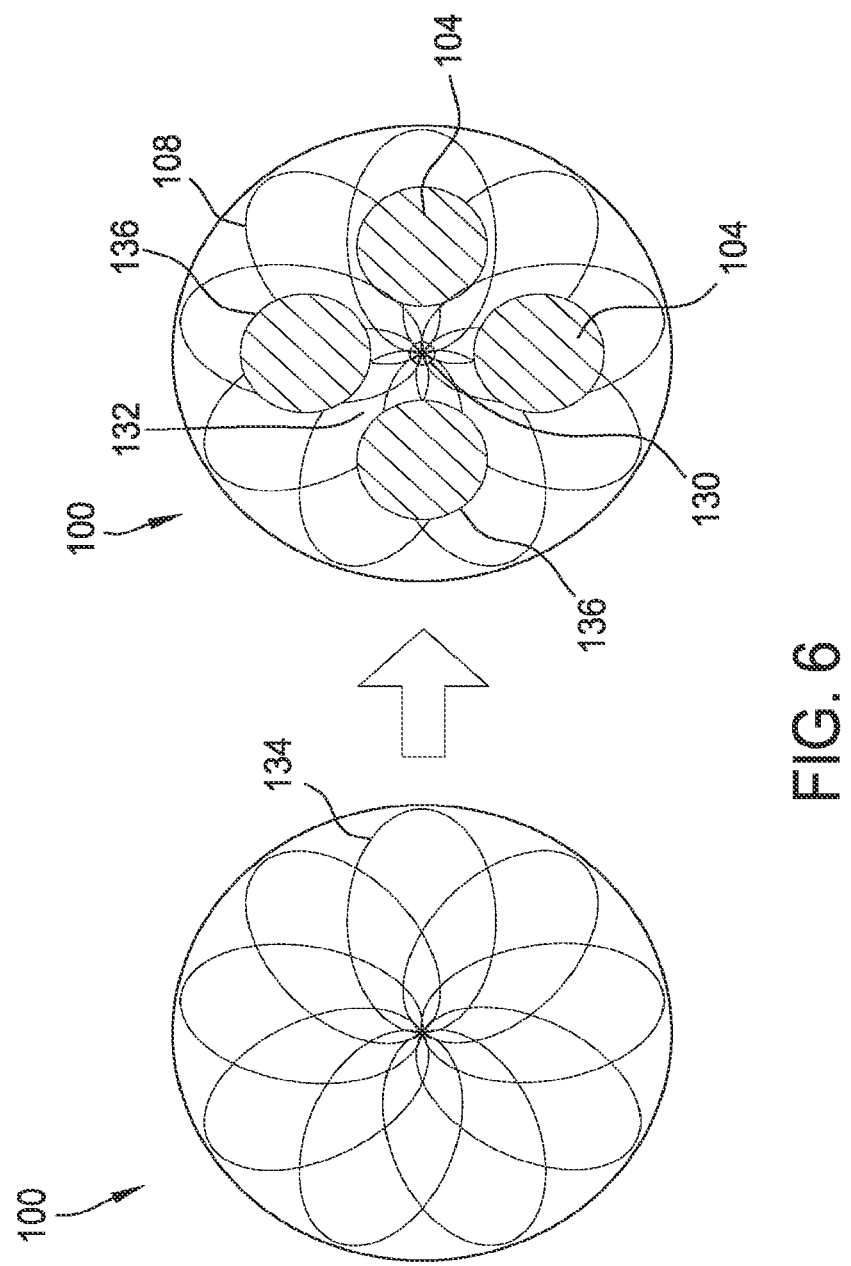
FIG. 6 depicts another exemplary embodiment of the occluder in accordance with the present disclosure.

In some embodiments, the attachment member 130 is coupled to the frame 102 via one or more spokes 132 extending radially inward from the radially inner surface 116 of one or more of the annular flanges 106, 108. The spokes 132 may be integrally formed with the frame 102 and/or may be attached to the frame 102 after the frame 102 is formed. In the embodiment illustrated in FIGS. 2A and 2B, the occluder 100 includes four spokes 132. The occluder 100 may include any suitable number of spokes 132, such as three, five, or more spokes 132. For example, in the embodiment illustrated in FIGS. 5A and 5B, the occluder 100 includes three spokes 132. The spokes 132 in this embodiment are integral with the frame 102 and formed from the same braided shape-alloy material of the frame 102. FIG. 6 illustrates a similar embodiment including four spokes 132. Integral spokes 132 may be formed by extending portions of the braided material (e.g., as shown in FIGS. 5A and 5B) or, in other embodiments, any material used to form the frame 102. Alternatively, integral spokes 132 may be formed by forming the corresponding annular flange (e.g., the proximal annular flange 108) as a fully closed disc 134 of material and cutting out portions therefrom to form the spokes 132 (e.g., as shown in FIG. 6). Although the embodiments illustrated in FIGS. 2A, 2B, and 5A-6 depict the spokes 132 positioned at the proximal angular flange 108, spokes 132 may be positioned at (e.g., extend from or be coupled to) the distal annular flange 106 and/or the waist member 110 without departing from the scope of the present disclosure. Moreover, spokes 132 may be substantially the same or may have differing lengths, shapes, orientations, and the like.

As described above, spokes 132 may be formed integrally with the frame 102, as continuations of the material of frame 102, or may be coupled to the frame 102. In some embodiments, spokes 132 may be formed from suture material, bio-absorbable material, and/or any suitable material. Spokes 132 may assist with recapture and/or re-positioning of the occluder 100 during deployment thereof. In some embodiments, the occluder 100 includes a reinforcement member (not shown) coupled to the radially inner surface 116 of an annular flange (e.g., the proximal annular flange 108) where the spokes 132 are coupled thereto. This reinforcement member may protect the closure 104 from the ends of the spokes 132, to prevent these ends of the spokes 132 from puncturing the closure 104. The reinforcement member may be formed from any suitable material, such as the same material of the closure 104 (e.g., a double layer of the closure material), or any other material.

In other embodiments, the attachment member 130 is coupled to the closure 104. For example, the attachment member 130 may be sewn, adhered, welded, and/or otherwise attached to the closure 104. In still other embodiments, the attachment member 130 may be formed integrally with the closure 104. For example, where the closure 104 is formed from a molded material, the attachment member 130 may be molded (e.g., as a threaded member or a hoop). In some embodiments, where the attachment member 130 is not attached to the frame 102, the occluder 100 may include no spokes, which may maximize the passageway 112 and enhance accessibility through the occluder 100 after deployment thereof.

Although the attachment member 130 is shown in a center of the occluder 100 in FIGS. 2A, 2B, and 5A-6, it should be readily understood that the attachment member 130 may be positioned in a non-central location without departing from the scope of the present disclosure.

In some embodiments in which the occluder 100 includes spokes 132 on the proximal annular flange 108, a closure 104 may be coupled to that proximal annular flange 108 via the spokes 132. For example, as shown in FIG. 6, the spokes 132 define through-holes 136 to the passageway 112, and each through-hole 136 has a corresponding closure 104 coupled thereacross. These closures 104 are coupled to the frame 102 along the spokes 132.

Turning now to FIG. 7, an occluder 100 in accordance with the present disclosure is shown within a delivery device 140. Specifically, the occluder 100 is shown in a collapsed configuration (where the occluder is shown in an expanded or deployed configuration in FIGS. 2A-6) within a delivery sheath 142. A delivery cable 144 is coupled to the attachment member 130 such that the occluder 100 may be advanced through the delivery sheath 142 to a target location for deployment (e.g., within an ASD). A similar embodiment is shown in FIG. 8. Specifically, the occluder 100 is collapsed and disposed within the delivery sheath 142. In this embodiment, the attachment member 130 is recessed within the frame 102. In some embodiments, a delivery device may further include a through-lumen or other such component that is configured to advance a distal end of the occluder 100, such as the distal annular flange 106, which may facilitate deployment and/or repositioning of the distal annular flange 106.

With reference now to FIGS. 9A-9C, another embodiment of an occluder 100 is illustrated. In this embodiment, the frame 102 is formed from a single layer of braided shape-alloy wire material (e.g., nitinol). The braided wire material is cut and terminated to form the frame 102 in a tube or doughnut-like shape. Methods for cutting, shaping, and forming such braided wire frames are described in further detail in International Patent Application Publication No. WO2018/204106, which is incorporated herein by reference in its entirety.

In this embodiment, the closure 104 is at least partially enclosed or folded within a pocket 150 formed by the distal annular flange 106, as depicted in FIG. 9A. The closure 104 may be folded within the distal annular flange 106 as the frame 102 is constructed (e.g., before the frame 102 is heat-set and/or cut), such as by being temporarily coupled to the material (e.g., the cut wire ends 152) forming the distal annular flange 106 before the distal annular flange 106 is heat-set into its final form. Alternatively, the closure 104 may be "installed" into the distal annular flange 106 after the frame 102 is formed (e.g., by inserting the outer edge of the closure 104 into the pocket 150). A separate closure 104 may be similarly coupled to the frame 102 within the proximal annular flange 108. Another closure 104 may be coupled to the frame 102 within the passageway 112 (e.g., coupled to the waist member 110).

As shown particularly in FIGS. 9B and 9C (which are a top and bottom view, respectively, of the occluder 100), the radially inner surface 116 of the annular flanges 106, 108 includes a scalloped edge including the cut wire ends 152. In some other embodiments, though not shown, at least some of these cut wire ends 152 may include eyelets or other attachment mechanisms that facilitate attaching the closure 104 thereto and/or that act as an attachment member 130 of the occluder 100 to facilitate advancement, recapture, an/or repositioning of the occluder 100 during deployment thereof.

Figure 21:
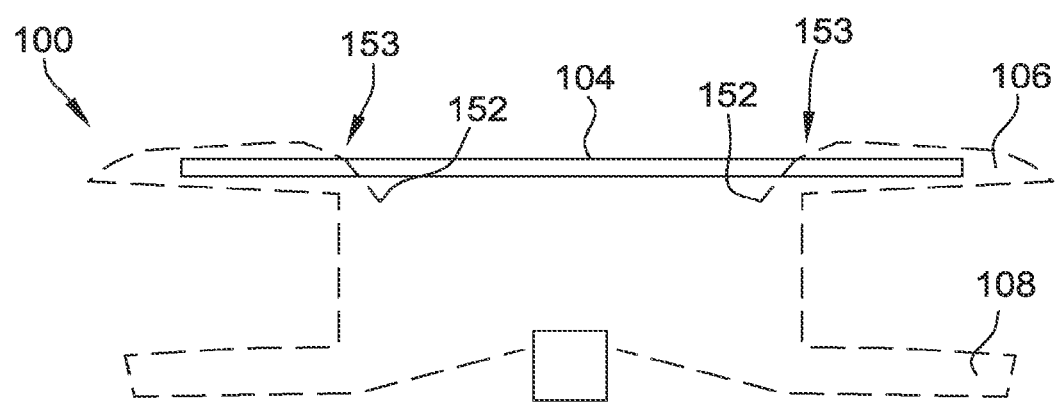
FIG. 21 illustrates another embodiment of an occluder in accordance with the present disclosure.

In some cases, the cut wire ends 152 of the frame 102 that form the radially inner surface 116 of the distal annular flange 106, as shown in FIGS. 9A and 9B, are exposed. To reduce a risk of thrombus from the cut wire ends 152, and to protect the cut wire ends 152 as the occluder 100 is deployed, the cut wire ends 152 may be fed through the closure 104, as shown in FIG. 21. For example, a slit 153 may be formed in the closure 104 through which cut wire ends 152 are positioned, such that the cut wire ends 152 are enclosed by the closure 104. In some such embodiments, the cut wire ends 152 may be subsequently sewn or otherwise coupled to the closure 104 to prevent relative movement between the closure 104 and the cut wire ends 152. The length of the cut wire ends 152 to be enclosed by the closure 104 and/or the tightness of the coupling of the cut wire ends 152 to the closure 104 may be selected to avoid interference with the ability of the frame 102 to collapse and expand.

As shown in FIG. 9C, the proximal annular flange 108 includes three spokes 132 that are coupled to the cut wire ends 152 and extend into the passageway 112. The attachment member 130 is coupled to the spokes 132 at a central location with respect to the proximal annular flange 108. Moreover, as best seen in FIG. 9A, the spokes 132 are oriented at an oblique angle with respect to the planar surface of the proximal annular flange 108, such that the attachment member 130 is recessed into the frame 102. In this embodiment, the spokes 132 define three equally-sized "access ports" 154 to the passageway 112.

Figure 10:
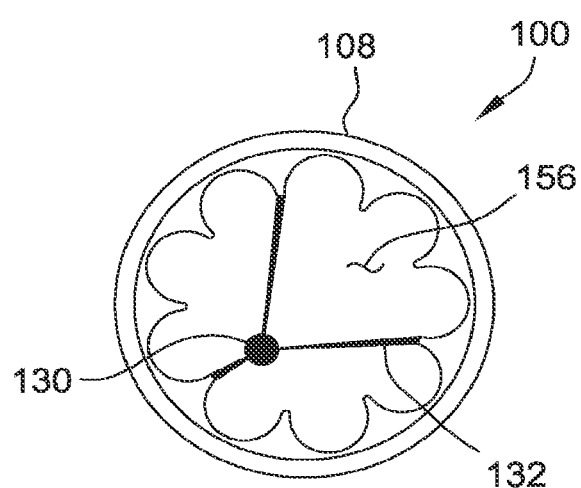
FIG. 10 is an alternative embodiment of the occluder shown in FIGS. 9A-9C.

An alternative embodiment of the occluder 100 is illustrated in FIG. 10. In this embodiment, the spokes 132 have different lengths and terminate at a non-central location with respect to the proximal annular flange 108. Accordingly, the attachment member 130 is coupled to the frame 102 at this non-central location. In this embodiment, the spokes 132 may interfere less with the passageway 112 by defining one access port 156 that is substantially larger than the access ports 154 (shown in FIG. 9C).

Figure 11:
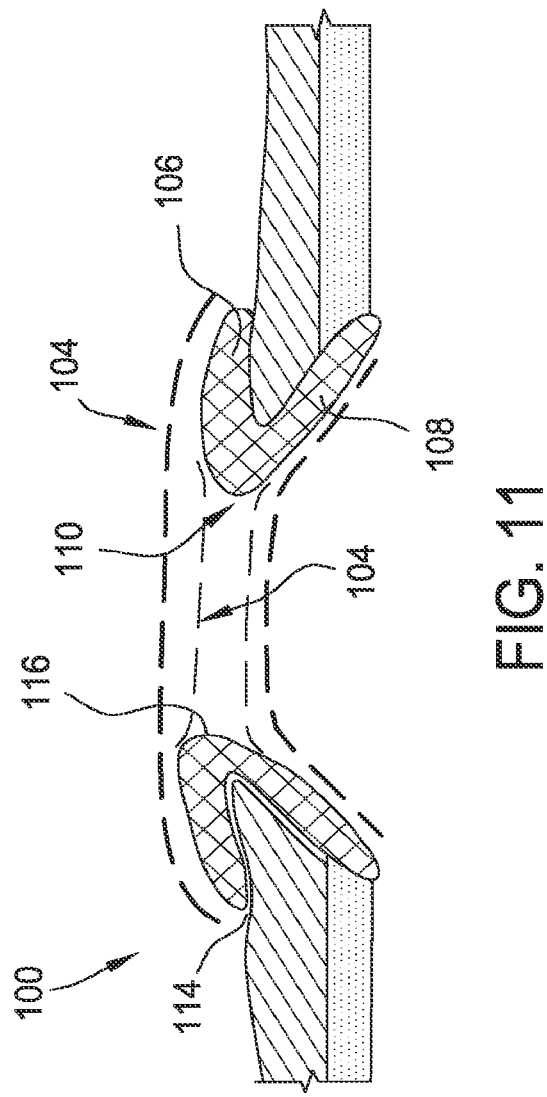
FIG. 11 is another exemplary embodiment of an occluder including an alternative frame shape in accordance with the present disclosure.

FIG. 11 depicts another embodiment of an occluder 100 in accordance with the present disclosure. In this embodiment, the waist member 110 forms an angle with respect to the distal annular flange 106, and the proximal annular flange 108 is not planar but concave. This alternative shape for the waist member 110 and the proximal annular flange 108 may promote endothelialization and/or integration into the tissue of the septal wall. One or more closures 104 may be coupled to the frame 102 at the outer surfaces of the annular flanges 106, 108 adjacent to the radially outer surface 114, as shown in dashed lines. Alternatively, closures 104 may be coupled to the frame 102 adjacent to the radially inner surface 116 of the annular flanges 106, 108, as shown in dotted lines.

Although the waist member 110 has been illustrated as conforming to the shape and/or size of the defect or tissue in which the occluder 100 is deployed, it is contemplated that the waist member 110 may be smaller than the defect and/or non-centrally located within the defect. In addition, the annular flanges 106, 108 may have alternative shapes and/or sizes than those shown herein, including irregular shapes and/or shapes that are not concentric or coaxial with the waist member 110. Moreover, the shape, size, and/or configuration of one annular flange 106, 108 may differ from that of the other annular flange 106, 108.

Figure 12A:
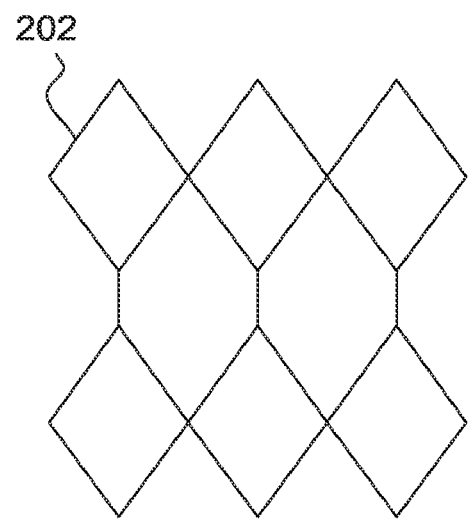
FIGS. 12A and 12B depict an alternative embodiment of the frame of the occluder.
Figure 12B:
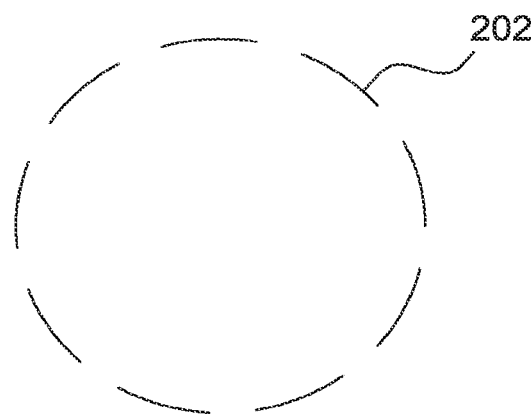
Figure 13A:
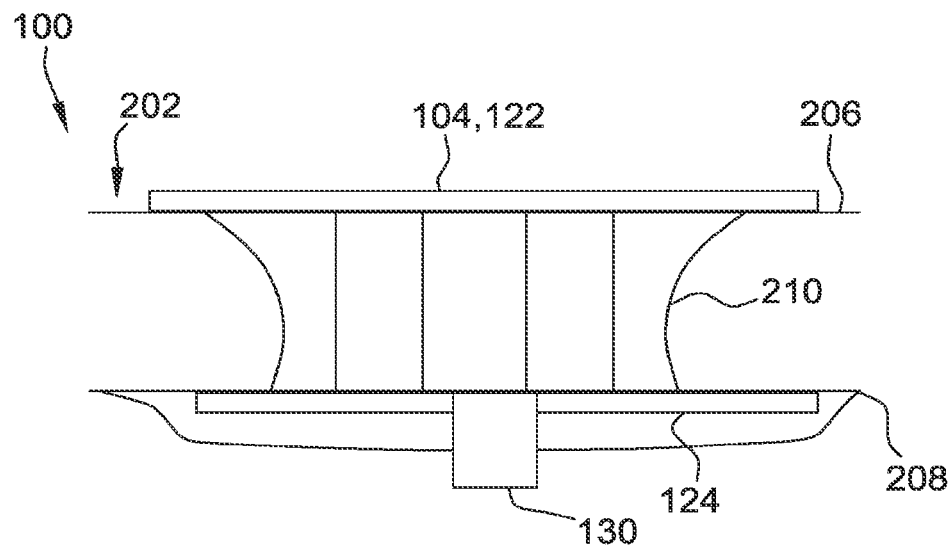
FIGS. 13A and 13B depict another alternative embodiment of the frame of the occluder.
Figure 13B:
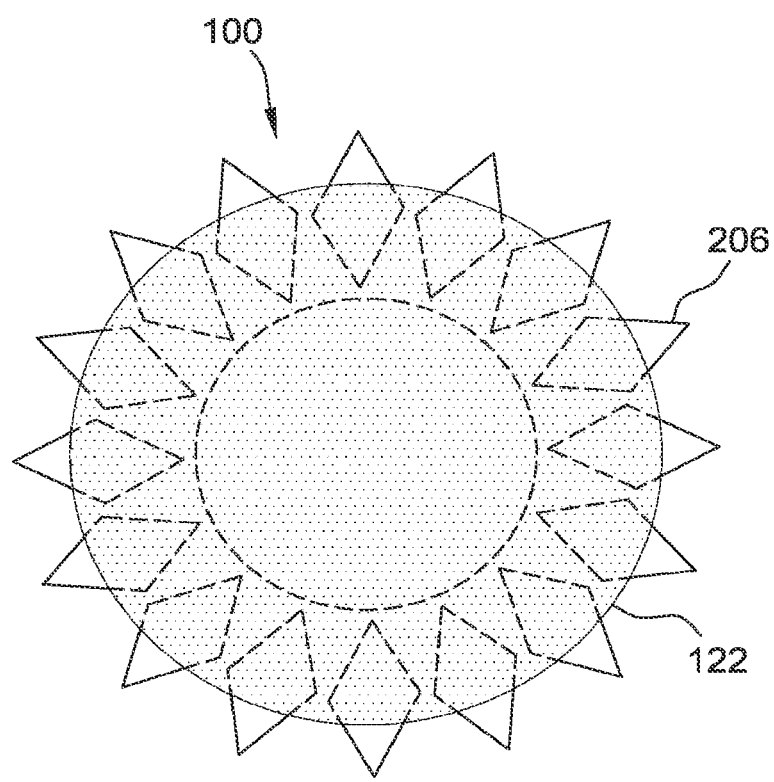

Turning now to FIGS. 12A-13B, an alternative embodiment of a frame 202 of the occluder 100 is shown. Specifically, the frame 202 is formed as a laser-cut frame (contrasted with a braided frame as previously shown). The frame 202 is first laser cut, as shown in FIGS. 12A and 12B (a side and top view, respectively), from a nitinol tube. The ends of the tube are then folded over to form flanges 206, 208 of the frame 202, as shown in FIGS. 13A and 13B (a side and top view, respectively). The flanges 206, 208 (as well as a waist member 210) are formed from a single layer of material, which may reduce the overall profile of the occluder 100. An attachment member 130 is coupled to the ends at the proximal annular flange 208. Closures 122, 124 are coupled to the flanges 206, 208.

Figure 14B:
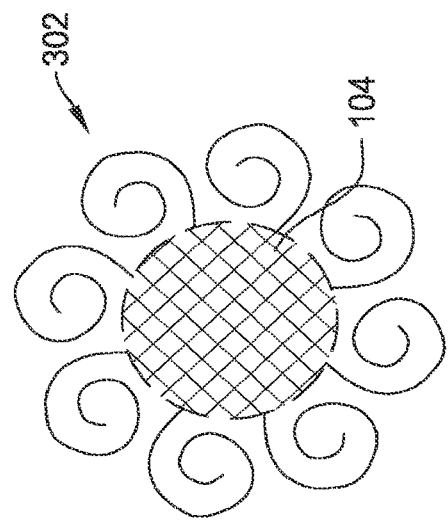
FIGS. 14A and 14B depict an alternative embodiment of an occluder including an alternative frame in accordance with the present disclosure.
Figure 14A:
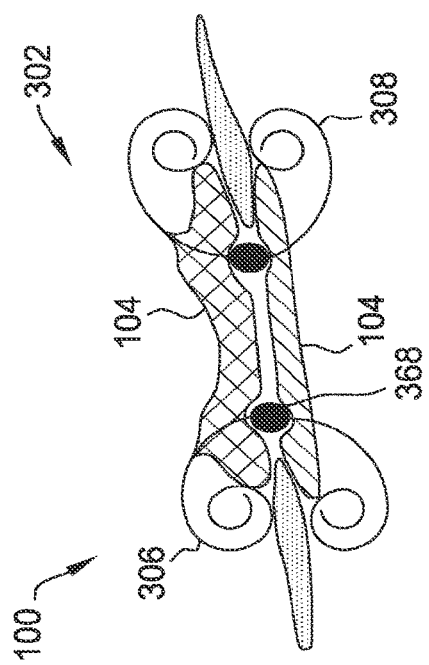
Figure 15B:
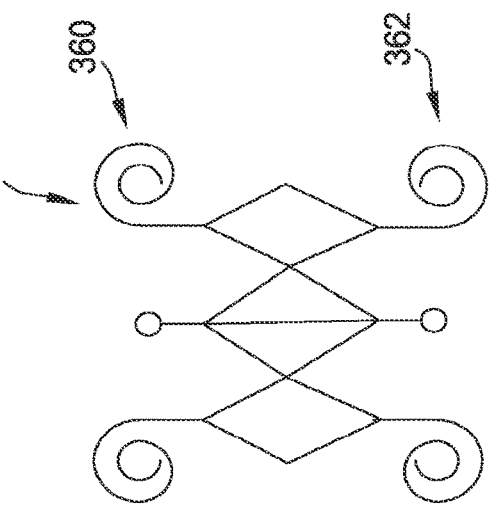
FIGS. 15A and 15B depict exemplary steps in a process of forming the occluder shown in FIGS. 14A and 14B.
Figure 15A:
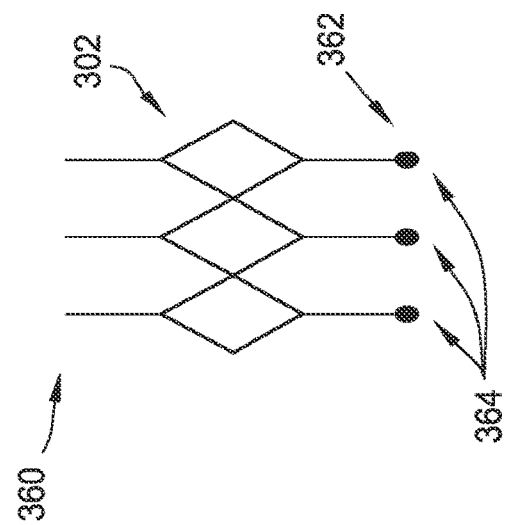

FIGS. 14A and 14B depict a side view and top view, respectively, of another occluder 100 in accordance with the present disclosure. The occluder 100 includes a frame 302 formed as a laser-cut frame, as described above, and/or from a plurality of wound wires. In this embodiment, annular flanges 306, 308 are formed from heat-set, curled, free wire ends. Specifically, the frame 302 may be formed as shown in FIGS. 15A and 15B. In particular, the frame 302 may include distal free wire ends 360 and proximal free wire ends 362. In some embodiments, the proximal free wire ends 362 may include attachment mechanisms 364, such as eyelets or hooks. As shown in FIG. 15B, the free wire ends 360, 362 are heat-set into curls. Closures 104 are coupled to the frame 302 at one or more longitudinal positions between annular flanges 306 and 308. For example, a distal closure 104 is coupled to the frame 302 generally adjacent to the distal annular flange 306, and a proximal closure is coupled to the frame 302 generally adjacent to the proximal annular flange 308.

Deployment of the occluder 100 shown in FIGS. 14A and 14B is depicted in FIGS. 16A-16C. As shown in FIG. 16A, the occluder 100 is collapsed and loaded into a delivery sheath 142. The distal free wire ends 360 may be coupled together within a delivery cap 366 to ensure they do not "curl up" within the delivery sheath 142. The delivery cap 366 is coupled to a first delivery cable 144A. The proximal free wire ends 362 may be gathered together and coupled to a second delivery cable 144B. Where the proximal free wire ends 362 include attachment mechanisms 364, those attachment mechanisms 364 may be engaged with the second delivery cable 144B for advancement and/or recapture of the occluder 100. The first and second delivery cables 144A, 144B may be coupled together and/or integral with one another.

To deploy the occluder 100 shown in FIGS. 14A and 14B, the delivery sheath 142 is maneuvered to a target location for the occluder 100 (e.g., an ASD). As the occluder 100 is advanced out of the delivery sheath 142, as shown in FIG. 16B, the distal free wire ends 360 are released from the delivery cap 366 (e.g., by manipulating the first delivery cable 144A), such that the distal free wire ends 360 are free to curl up into their heat-set configuration. The delivery sheath 142 is retracted, and the distal free wire ends 360 engage the tissue of the septal wall to keep the occluder 100 in place. As the delivery sheath 142 is retracted further, as shown in FIG. 16C, the proximal free wire ends 362 are released (e.g., by manipulating the second delivery cable 144B) and curl up into their heat-set configuration. Accordingly, the distal free wire ends 360 form the distal annular flange 306, and the proximal free wire ends 362 form the proximal annular flange 308 of the occluder 100.

One or more closures 104 may be coupled to the frame 302 as shown in FIGS. 14 and 16A-16C. In addition, in some embodiments, such as where the frame 302 is formed from a polymeric and/or non-radiopaque material, the occluder 100 may further include radiopaque markers 368 coupled to the frame 302.

Figure 17A:
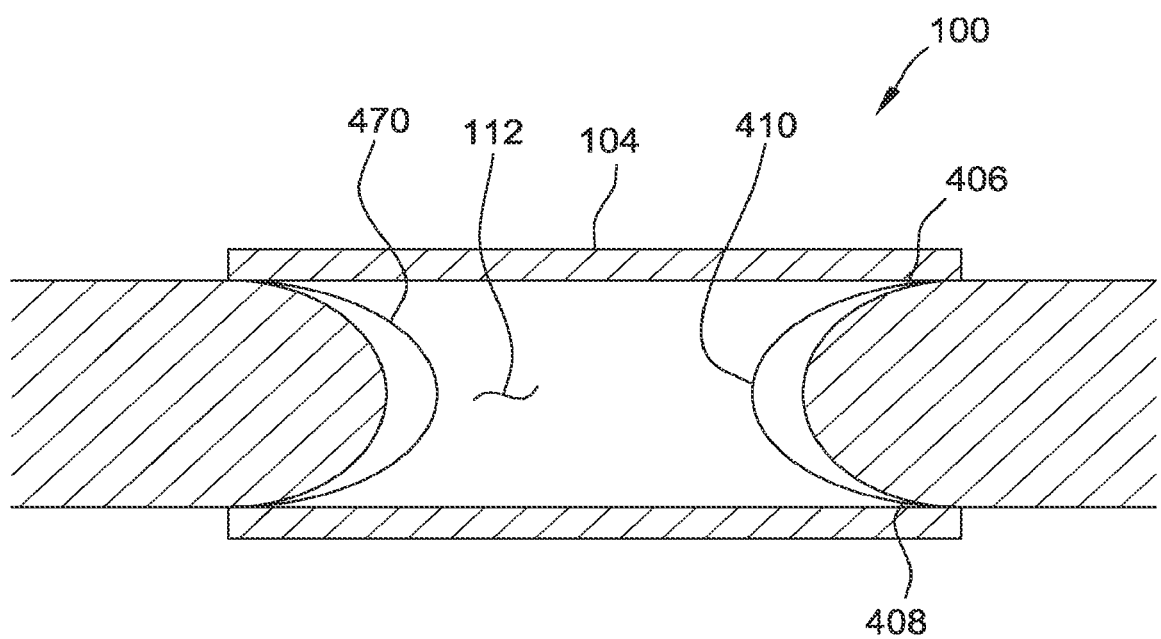
FIGS. 17A and 17B illustrate an alternative embodiment of an occluder including an alternative frame in accordance with the present disclosure.
Figure 17B:
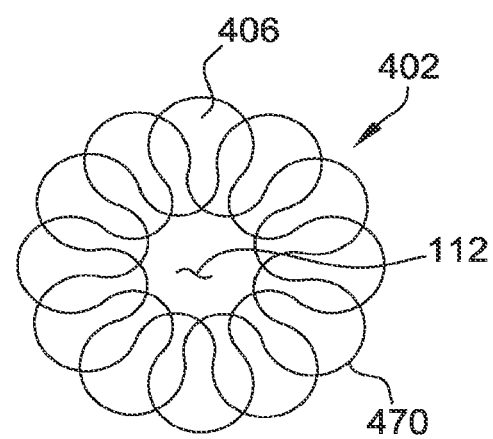
Figure 19:
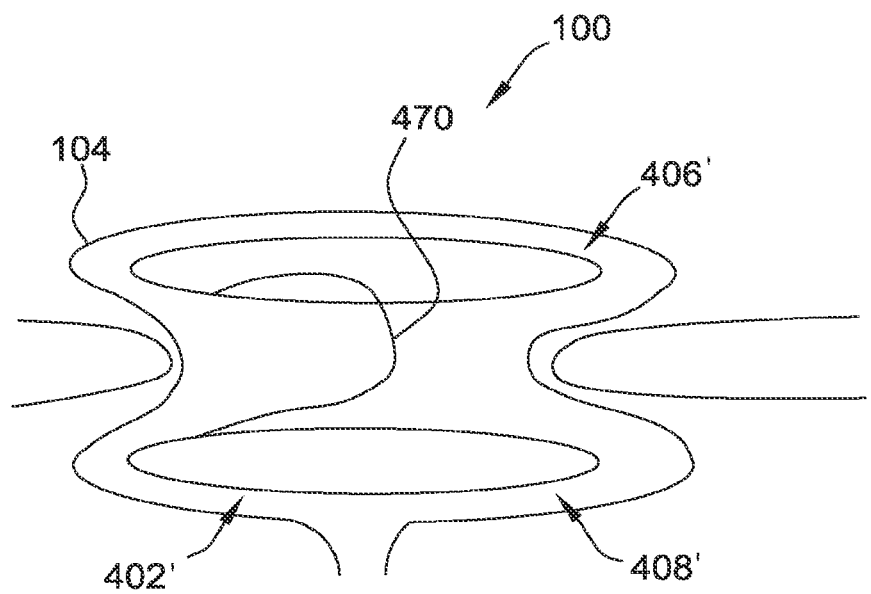
FIG. 19 illustrates another embodiment of an occluder in accordance with the present disclosure.

Yet another alternative embodiment of the occluder 100 is illustrated in FIGS. 17A and 17B (a side and top view, respectively, of the occluder 100). A frame 402 of the occluder 100 is formed from one or more wound wires 470 that are continuously looped about a mandrel and heat-set. Therefore, annular flanges 406, 408 and a waist member 410 of the frame 402 are defined by a plurality of loops of the wound wire(s) 470. Alternatively, as shown in FIG. 19, a frame 402' may include annular flanges 406', 408' formed from only a single loop of wound wire 470.

Closure(s) 104 are coupled to the frame 402/402', as described above herein. In some such embodiments, one or more of the wires 470 may be wound into the passageway 112 to form an attachment member. Alternatively, an attachment member may be coupled to the frame 402/402' as described herein.

Figure 20:
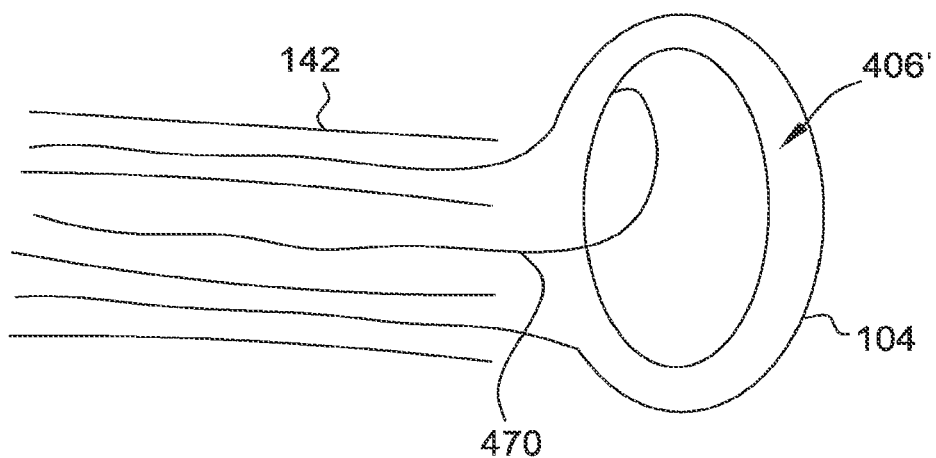
FIG. 20 illustrates deployment of the occluder shown in FIG. 19.

FIG. 18 illustrates the occluder 100 shown in FIG. 17 in a collapsed configuration within a delivery sheath 142. FIG. 20 illustrates the occluder 100 shown in FIG. 19 in a partially collapsed configuration as the occluder 100 is advanced from a delivery sheath 142 to a target location (e.g., an ASD).

It should be understood that any feature of any embodiment disclosed herein may be combined with any other feature. For example, a hybrid frame may include both laser-cut and braided or wound-wire features coupled together.

In addition, although the occluders of the present disclosure have been described as being suitable for deployment within ASDs, these occluders are suitable for deployment in other tissue and/or defects, including for use for fenestrated ASDs, VSDs, and/or atrial shunting.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An occluder for occluding an atrial septal defect ("ASD") within an atrial septal wall, the occluder comprising:
a self-expanding mesh frame formed of braided wires of nitinol, the frame including (i) a distal annular flange having a radially outer surface and a radially inner surface, the distal annular flange configured to be positioned with a left atrium and to engage a distal surface of the atrial septal wall, (ii) a proximal annular flange having a radially outer surface and a radially inner surface, the proximal annular flange configured to be positioned within a right atrium and to engage a proximal surface of the atrial septal wall, and (iii) a waist member extending between and connecting the distal annular flange to the proximal annular flange, the waist member configured to engage a surface of the ASD; and
a fabric closure formed of polyethylene terephthalate,
wherein the radially inner surface of the distal annular flange, the waist member, and the radially inner surface of the proximal annular flange define an access passage through the mesh frame, and the fabric closure is connected to the waist member and positioned radially inward of the waist member to (i) restrict bodily fluids from passing through the access passage and to (ii) enable subsequent access through the access passage when the occluder is deployed within the ASD,
wherein the mesh frame includes a plurality of spokes extending radially inwardly from the radially inner surface of the proximal annular flange, the plurality of spokes coupled to an attachment member, the attachment member configured to couple the occluder to a delivery device,
wherein the plurality of spokes define a plurality of access ports leading to the access passage, the plurality of access ports being sized to accommodate medical devices having a diameter of 4 Fr to 36 Fr.

2. The occluder of claim 1, wherein the occluder includes only one fabric closure.

3. The occluder of claim 2, wherein the fabric closure is circular.

4. The occluder of claim 1, wherein the mesh frame is formed with two layers of braided wires of nitinol.

5. The occluder of claim 1, wherein the proximal annular flange, the distal annular flange, and the waist member are integral with each other.

6. The occluder of claim 5, wherein the plurality of spokes are formed non-integrally with the mesh frame.

7. The occluder of claim 5, wherein the plurality of spokes are formed integrally with the mesh frame.

8. The occluder of claim 7, wherein the plurality of spokes are formed of the braided wires of nitinol that form the mesh frame.

9. The occluder of claim 8, wherein the plurality of spokes are formed by extending portions of the braided wires of nitinol radially inwardly from the proximal annular flange.

10. The occluder of claim 1, wherein the attachment member is positioned at a radial center of the occluder.

11. The occluder of claim 10, wherein the attachment member is a screw member with threads.

12. The occluder of claim 1, wherein a diameter of the radially outer surface of the distal annular flange is at least 5 mm larger than a diameter of the access passage.

13. The occluder of claim 1, wherein the radially inner surface of the distal annular flange, the waist member, and the radially inner surface of the proximal annular flange define the access passage to accommodate the medical devices.

14. The occluder of claim 1, wherein an unobstructed area of the distal annular flange delimiting the access passage and defined by the radially inner surface of the distal annular flange represents between 50% and 70% of a total surface area defined by the radially outer surface of the distal annular flange.

15. The occluder of claim 14, wherein an unobstructed area of the proximal annular flange delimiting the access passage and defined by the radially inner surface of the proximal annular flange represents between 50% and 70% of a total surface area defined by the radially outer surface of the proximal annular flange.

16. The occluder of claim 1, wherein the fabric closure is connected to the waist member via sutures.

17. The occluder of claim 1, wherein the fabric closure is trapped within the mesh frame.

18. The occluder of claim 1, wherein the plurality of spokes includes three spokes.

19. The occluder of claim 1, wherein the plurality of spokes includes more than five spokes.

* * * * *